United States Patent

Kraus et al.

[11] 4,347,054
[45] Aug. 31, 1982

[54] ORTHODONTIC EXPANSION SCREW

[75] Inventors: Hans-Joachim Kraus, Waldbronn; Berthold Walter, Remchingen-Wi, both of Fed. Rep. of Germany

[73] Assignee: Dentaurum H.P. Winkelstroeter KG, Ispringen, Fed. Rep. of Germany

[21] Appl. No.: 887,955

[22] Filed: Mar. 20, 1978

[30] Foreign Application Priority Data

Mar. 23, 1977 [DE] Fed. Rep. of Germany ....... 2712696

[51] Int. Cl.³ .............................................. A61C 7/00
[52] U.S. Cl. ..................................................... 433/7
[58] Field of Search ................ 32/14 E, 64, 61; 433/7

[56] References Cited

U.S. PATENT DOCUMENTS

| 3,800,420 | 4/1974 | Quaknine | 32/14 E |
| 3,832,778 | 9/1974 | Wallshein | 433/7 |
| 3,835,540 | 9/1974 | Biederman | 32/14 E |
| 3,921,294 | 11/1975 | Wallshein | 32/14 E |
| 4,026,023 | 5/1977 | Fisher | 433/7 |
| 4,107,843 | 8/1978 | Spino et al. | 433/7 |

FOREIGN PATENT DOCUMENTS

| 352360 | 4/1922 | Fed. Rep. of Germany | 433/7 |
| 153604 | 11/1940 | Fed. Rep. of Germany | 433/7 |
| 698507 | 11/1940 | Fed. Rep. of Germany | 433/7 |
| 1081189 | 10/1960 | Fed. Rep. of Germany | 433/7 |
| 1939221 | 5/1963 | Fed. Rep. of Germany | |
| 1876628 | 3/1966 | Fed. Rep. of Germany | |
| 1312975 | 11/1962 | France | 433/7 |
| 668227 | 3/1952 | United Kingdom | 433/7 |

OTHER PUBLICATIONS

*Dental Labor*, German periodical, 7-1972, pp. 27-31.

*Primary Examiner*—Gene Mancene
*Assistant Examiner*—Michael J. Foycik
*Attorney, Agent, or Firm*—Neuman, Williams, Anderson & Olson

[57] ABSTRACT

An orthodontic expansion screw is provided having two screw bodies which are displaceable relative to each other by a screw spindle. A guide pin disposed parallel to the spindle is attached to an attachment section of one of the screw bodies and engages a guide bore of the second screw. The screw spindle has threaded sections of counter-rotating threads which engage threaded bores in the screw bodies; such opposed sections extend from an actuating section to which attached. The second screw body has a guide portion which extends from the second screw body portion. The first screw body has a threaded body portion extending from the attachment section whereby maximum separation of the screw bodies is permitted by virtue of the extended threaded bore.

8 Claims, 2 Drawing Figures

ORTHODONTIC EXPANSION SCREW

The invention relates to an orthodontic expansion screw comprising two screw bodies which are displaceable relative to each other by means of a screw spindle and at least one guide pin extending parallel to the latter, said guide pin being attached to an attachment section of the first of the two screw bodies and engaging a guide bore of the second screw body, said screw spindle comprising on either side of an actuating section threaded sections with counter-rotating threads engaging threaded bores in both screw bodies, said second screw body comprising a guide portion which prolongs its guide bore, said guide portion extending beyond the part of the second screw body accommodating its threaded bore in the direction of the first screw body.

Such expansion screws are used to stretch the midpalatal suture in order to correct dental misplacement. A first type of orthodontic expansion screw is embedded in a synthetic resin plate together with clamps which engage the teeth. The synthetic resin plate is divided parallel to the midpalatal suture so that the two screw bodies of the expansion screw lie on different sides of the dividing slit in the synthetic resin plate. A second type of orthodontic expansion screw comprises four so-called retention arms which are formed by stiff wires whose first ends are soldered to the screw bodies, while the other ends protruding from the expansion screw are secured to bands which are preformed into rings.

The latter are placed around teeth located on either side of the midpalatal suture. It is particularly narrow jaws that require particularly wide expansion of the midpalatal suture and so expansion screws which enable wide expansion, i.e., expansion screws whose screw bodies can be moved particularly far apart from each other with the help of the screw spindle would be required. To meet this demand in the known expansion screws the housing formed by the two screw bodies must be relatively long (measurement of the screw housing in the longitudinal direction of the guide pins or of the screw spindle when the expansion screw is closed), but on the other hand, particularly narrow jaws do not provide sufficient room for accommodating expansion screws having a particularly long housing.

Orthodontic expansion screws of the first aforementioned kind comprising guide pins on either side of the screw spindle are already known. The guide pins in these orthodontic expansion screws are prevented from sliding out of the guide bores prematurely by providing the screw body which accommodates the guide bores with extensions on either side of the screw spindle in the region of the guide bores. These extensions protrude in the direction of the other screw body and enable guide bores to be prolonged. The other screw body supporting the guide pins comprises a planar internal end face which the two extensions of the other screw body abut when the expansion screw is closed. In spite of this measure several expansion screws with housings of differing length were still required in practical application, so as to have, on the one hand, expansion screws which can be accommodated in particularly narrow jaws, and on the other hand, orthodontic expansion screws which enable particularly wide expansion. When expanding the midpalatal suture of a particularly narrow jaw, the orthodontist first of all made and inserted a device wherein a particularly short orthodontic expansion screw is used. After the midpalatal suture had been expanded to a certain extent a second device with an expansion screw having a longer housing and therefore enabling greater maximum expansion had to be made and inserted. This hitherto existing practice is not only expensive but also disadvantageous because such devices must be fitted and therefore cannot be exchanged within a very short time. The jaw is, however, particularly prone to shrink again when the pressure which was previously exerted by the device is removed. The expansion of the midpalatal suture which was attained is therefore lost again at least partly when the device is exchanged.

The object underlying the invention was to develop an orthodontic expansion screw which permits greater maximum expansion than the known expansion screws having housings of the same length. Departing from an orthodontic expansion screw of the first aforementioned kind, this object is attained in accordance with the invention by the first screw body being provided with a threaded portion which prolongs its threaded bore. This threaded portion extends beyond its attachment section for the guide pin in the direction of the second screw body. When the basic concept of the invention is applied, the guide bore of the second screw body can be prolonged to almost the entire length of the screw housing without having the disadvantage of hitherto known expansion screws, namely that the threaded bore in the first screw body is correspondingly shortened.

There are embodiments of expansion screws comprising retention arms wherein the ends of the retention arms on one side extend into the guide bores of the second screw body and are attached there. As the guide length for the guide pins is thereby shortened, it is also known to weld the retention arms to the longitudinal sides of the expansion screw housing. However, the welding causes a relatively large area of the retention arms to be heated so strongly that they are often too brittle for later use and therefore tend to break off. In order to maintain the full guide length in an inventive expansion screw comprising retention arms, at least the retention arms attached to the second screw body are attached to the outside of the screw bodies by Laser welded seams. Laser welding enables the heat required to bond the materials together to be limited to a very narrow area, thus eliminating undesired embrittlement of the retention arms.

In the following the invention is described in detail on the basis of an embodiment of a known orthodontic expansion screw and a preferred embodiment of an inventive orthodontic expansion screw.

Figure 1:
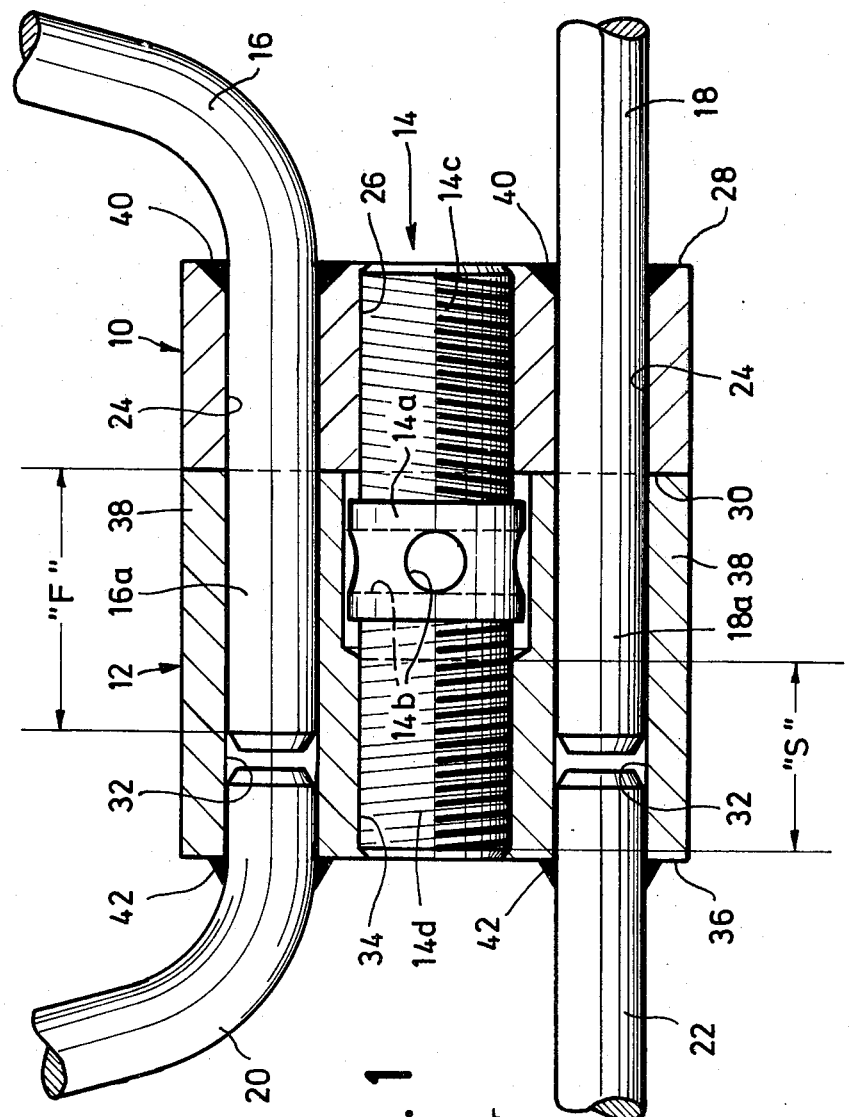
FIG. 1 is a section through a known orthodontic expansion screw comprising retention arms.

The known orthodontic expansion screw shown in FIG. 1 comprises a housing consisting of two screw bodies 10 and 12, a screw spindle designated in its entirety 14 and four rod-shaped retention arms 16, 18, 20 and 22, two of these, namely retention arms 16 and 18, each constituting one guide pin 16a and 18a. The first screw body 10 comprises two simple bores 24 and a threaded bore 26, all extending from an external end face 28 to an internal end face 30, and both end faces being planar and parallel to each other. The second screw body 12 likewise comprises two simple bores 32 and a threaded bore 34 which extend from an outer end face 36 inwardly. The threaded bore 34 is, however, shorter than the simple bores 32, as two guide portions 38 which extend beyond the inside end of the threaded bore 34 in the direction of the screw body 10 are provided as integral parts of the screw body 12 for these simple bores. The retention arms 16 and 18 are soldered to the first screw body 10 at 40, but glide with their guide pins 16a and 18a in the bores 32 of the other screw body 12, while only a short piece of the retention arms 20 and 22 extends into the bores 32 of the screw body 12 and the retention arms 20 and 22 are soldered to this screw body at 42. The screw spindle 14 comprises at its center a spindle head 14a having transverse bores 14b. On either side of the spindle head there are threaded sections 14c and 14d, which like the threaded bores 26 and 34 have counter-rotating threads, so that rotation of the screw spindle 14 in one direction causes both screw bodies 10 and 12 and with them the retention arms 16 and 18, on the one hand, and 20 and 22, on the other hand, to be moved away from one another in opposite directions.

It is clearly apparent that the bores 32 and the guide pins 16a and 18a would permit an expansion "F", which, however, cannot be achieved owing to the fact that even after a slighter expansion, namely after reaching an expansion "S", the screw spindle 14 falls out of the threaded bores 26 and 34. Furthermore, it is apparent that the expansion attainable by way of the guide pins and the guide bores could be even further increased by securing the retention arms 20 and 22 to the outside of the housing, prolonging the guide pins 16a and 18a as far as the external end face 36 of the second screw body 12 and finally further shortening the first screw body 10 and further lengthening the guide portions 38, however, all these measures would be of no avail because the screw connection between the two screw bodies does not permit greater expansion.

Figure 2:
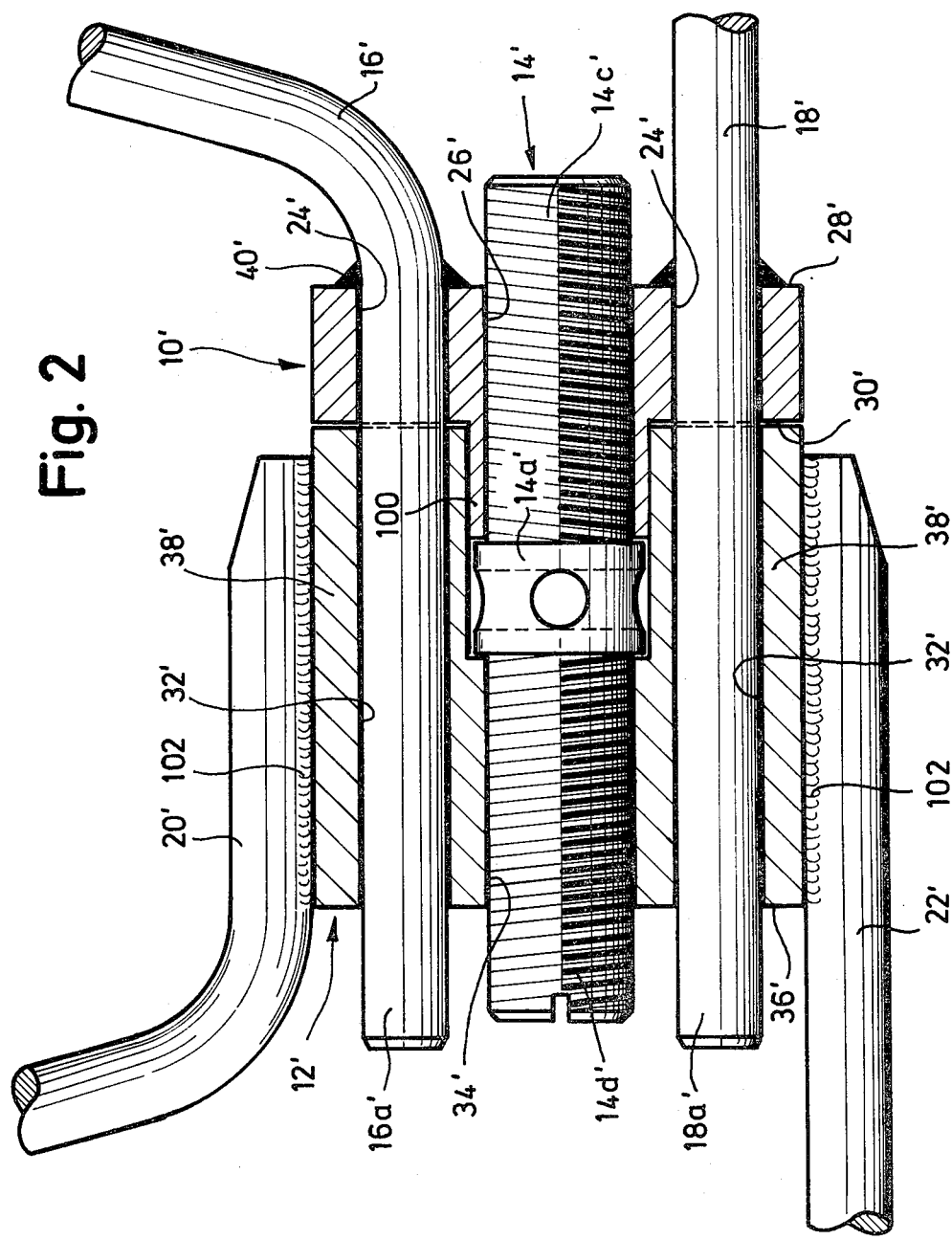
FIG. 2 is a corresponding section through an inventive orthodontic expansion screw comprising retention arms.
Figure 3:
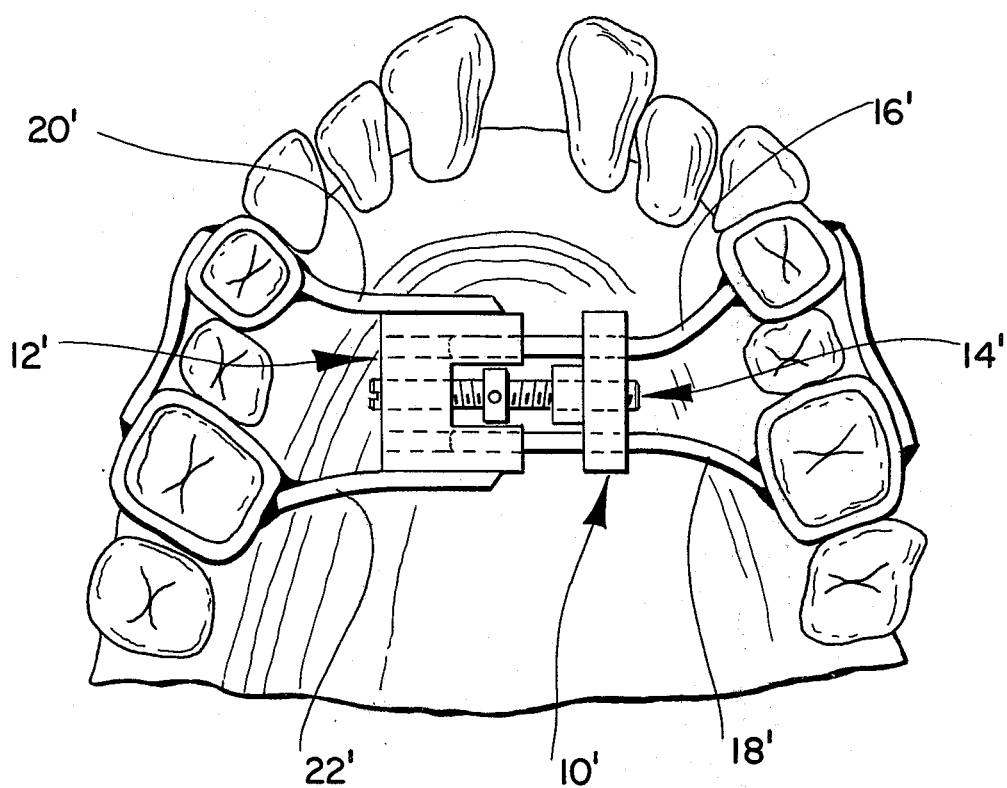

As is evident from FIG. 2, the invention remedies this situation. The various parts of the inventive orthodontic expansion screw shown in FIG. 2 have been given the same reference characters as in FiG. 1 only with a prime added thereto, and so it will not be necessary to describe features of the orthodontic expansion screw shown in FIG. 2 which correspond to the embodiment shown in FIG. 1. The inventive orthodontic expansion screw does, however, differ from the prior art as shown in FIG. 1 in two important ways:

The first screw body 10' does not have a planar internal end face, but rather a graduated internal end face 30', as its threaded bore 26' protrudes beyond its simple bores 24' in the direction of the second screw body 12' owing to a threaded portion 100 and engages between the guide portions 38' of the second screw body 12'. Owing to this measure the guide portions 38' can be made long enough for the length of the simple bores 24' in the first screw body 10' to be sufficient to give the retention arms 16' adequate support without the threaded bore 26' in the first screw body 10' having to be shortened as was the case in the prior art. Furthermore, the threaded portion 100 enables the entire length of the threaded section 14c' of the screw spindle 14' to be used, which was hitherto not the case owing to the planar internal end face 30 of the first screw body 10.

In accordance with the invention, the retention arms 20' and 22' are secured to the longitudinal sides of the second screw body 12' by Laser welded seams 102. The full length of the bores 32' of the screw body 12' is therefore available as guide length for the guide pins 16a' and 18a', and in addition, the hardness of the retention arms is maintained as only very small areas of material are heated during Laser welding.

We claim:

1. An orthodontic expansion screw comprising a first body section having a projecting portion of reduced cross-sectional area extending from a body portion of larger cross-sectional area and having a theaded bore extending through said body portions; said body portions being integrally formed in a single unit; a second body section having a relieved portion for receiving said first section projecting portion in overlapping relation; said second section having a portion defining a threaded bore in axial alignment with said relieved portion; at least one guide pin attached to said first body section, said second body section having a guide bore for receiving said guide pin and having a projecting guide portion which prolongs its guide bore; said guide portion extending beyond the threaded bore of said second body section in the direction of said first body section; said relieved portion and threaded bore portion of said second section being integrally formed in a single unit; spindle means threadedly engaging said threaded bores of said first and second body sections for effecting relative movement between said screw sections; said threaded bore in said screw first body section projecting portion enabling said first body section to be moved along the length of said spindle means a distance greater than the length of said bore in said first body section portion of larger sectional area in the course of effecting movement of said first body section relative to said second body section; retention means connected to each screw body section for retainin said screw body sections relative to teeth of a user of said screw.

2. An orthodontic expansion screw comprising a screw body with a first body section having an attachment portion and a second body section; said first and second body sections having threaded bores; a screw spindle threadedly engaging said bores of said body sections for effecting displacement of said sections relative to each other; at least one guide pin attached to said attachment portion of said first body section; said second body section having a guide bore for receiving said guide pin; said spindle having threads of opposite hand comprising spindle sections extending in opposite directions relative to the spindle center; said second body section having a projecting guide portion which prolongs its guide bore; said guide portion extending beyond the threaded bore of said second body section in the direction of said first body section; the length of said attachment portion being a fraction of the length of one of the threaded sections of said spindle; said first body section including a projecting threaded portion which prolongs its threaded bore and extends beyond its attachment portion in the direction of the second body section whereby the projecting threaded portion of the first body section extends adjacent the inner end of the spindle threads engaging the same and extends over and overlaps said projecting guide portion of the second body section when the threaded sections of said spindle are fully screwed into the threaded bores of the body sections; the threaded bore portion of said first body portion threadedly engaging said spindle in the course of moving said body sections away from each other whereby said screw sections may be moved apart a distance greater than the length of said attachment portion; retention means connected to each screw body section for retaining said screw body sections relative to teeth of a user of said screw.

3. The orthodontic expansion screw as set forth in claim 2 in which a guide pin is disposed on either side of said screw spindle and four retention arms are attached to the screw body sections via attachment sections extending parallel to the guide pins; at least the retention arms attached to the second screw body section being fixed to the outside of said second screw body section.

4. The orthodontic expansion screw as set forth in claim 2 in which said spindle head is simultaneously disposed adjacent said projecting threaded portion of said first body section and adjacent the innermost portion of said projecting guide portion of said second body section when said screw spindle is fully screwed into the threaded bores of said body sections.

5. The orthodontic expansion screw of claim 2 in which said projecting guide portion of said second body section is integrally formed with the remainder of said second body section, and said projecting threaded portion of said first body section is integrally formed with the remainder of said first body section.

6. The orthodontic expansion screw of claim 1 or claim 2 in which the overlapping engagement of said body sections comprises a telescopic engagement.

7. The expansion screw of claim 1 or 2 in which said retention means attached to said first body section is integrally formed with said at least one guide pin.

8. An orthodontic expansion screw comprising a first body section having a projecting portion of reduced sectional area extending from a body portion of larger sectional area and having a threaded bore extending through both of said body portions; a guide pin attached to said first body section portion of larger sectional area; said screw having a second body section including a first portion with a guide bore for receiving said guide pin; said first portion projecting outwardly relative to a second portion having a threaded bore; spindle means having threads of opposite hand for threadedly engaging said threaded bores of said first and second body sections and effecting relative movement between said screw body sections; said projecting first portion of said second body section also having a surface portion interposed said spindle means and guide bore for receiving said screw first section projecting portion in overlapping relationship; said threaded bore in said screw first body section projecting portion enabling said first body section to be threadedly moved along the length of said spindle means a distance greater than the length of said bore in said body portion of larger sectional area in the course of effecting movement of said screw first body section relative to said second body section.

* * * * *